(12) United States Patent
Hino et al.

(10) Patent No.: US 7,560,601 B2
(45) Date of Patent: Jul. 14, 2009

(54) METHOD FOR PRODUCING 3-METHYL-1,5-PENTANEDIOL

(75) Inventors: Kenichi Hino, Tokyo (JP); Kazuyuki Yada, Ibaraki (JP); Keisuke Saeki, Tokyo (JP)

(73) Assignee: Kuraray Co., Ltd., Okayama (JP)

( * ) Notice: Subject to any disclaimer, the term of this patent is extended or adjusted under 35 U.S.C. 154(b) by 0 days.

(21) Appl. No.: 12/298,549

(22) PCT Filed: Apr. 24, 2007

(86) PCT No.: PCT/JP2007/058835

§ 371 (c)(1),
(2), (4) Date: Oct. 27, 2008

(87) PCT Pub. No.: WO2007/125909

PCT Pub. Date: Nov. 8, 2007

(65) Prior Publication Data

US 2009/0099392 A1    Apr. 16, 2009

(30) Foreign Application Priority Data

Apr. 28, 2006   (JP)   ............................. 2006-125269

(51) Int. Cl.
*C07C 29/132*   (2006.01)
*C07C 29/151*   (2006.01)
*C07C 29/153*   (2006.01)

(52) U.S. Cl. .................. 568/865; 568/866; 568/867
(58) Field of Classification Search ................ 568/865, 568/866, 867
See application file for complete search history.

(56) References Cited

FOREIGN PATENT DOCUMENTS

| JP | 57045120 | 3/1982 |
| JP | 61172838 | 8/1986 |
| JP | 61249940 | 11/1986 |
| JP | 61249941 | 11/1986 |
| JP | 1100139 | 4/1989 |
| JP | 11236341 | 8/1999 |

*Primary Examiner*—Elvis O Price
(74) *Attorney, Agent, or Firm*—Lucas & Mercanti, LLP

(57) ABSTRACT

Provided is a method for producing 3-methyl-1,5-pentanediol by hydrogenating 2-hydroxy-4-methyltetrahydropyran in the presence of a hydrogenation catalyst, characterized in that the hydrogenation is further carried out in the presence of a basic compound. By this method, in producing MPD by hydrogenation of MHP, high-purity MPD can be produced by effectively suppressing generation of by-products such as MPAE and MVL even when a known hydrogenation catalyst is used.

1 Claim, 1 Drawing Sheet

METHOD FOR PRODUCING 3-METHYL-1,5-PENTANEDIOL

TECHNICAL FIELD

The present invention relates to a method for producing 3-methyl-1,5-pentanediol (hereinafter, referred to as "MPD"). The MPD obtained by the present invention is useful as a raw material of various polymers such as polyester and polyurethane.

BACKGROUND ART

The conventional method for producing MPD includes, for example, a method where 3-methyl-3-butene-1-ol (hereinafter, referred to as "IPEA") is reacted with carbon monoxide and hydrogen in the presence of a rhodium compound to obtain 2-hydroxy-4-methyltetrahydropyran (hereinafter, referred to as "MHP"), which is then hydrogenated under an acidic condition in the presence of water and a hydrogenation catalyst (see Patent Literatures 1 and 2) and a method where the MHP is hydrogenated in the presence of Raney nickel modified with molybdenum (see Patent Literature 3).
Patent Literature 1: JP-A-60-202835
Patent Literature 2: JP-A-61-249940
Patent Literature 3: JP-A-1-100139

DISCLOSURE OF INVENTION

Problem to be Solved by the Invention

The present inventors carried out the production of MPD by hydrogenating MPH continuously in the presence of the same catalyst according to the method disclosed in Patent Literature 1 or 2. The amount of by-products in the reaction solution, that is, the compound represented by the following formula (hereinafter, referred to as "MPAE"):

[Formula 1]

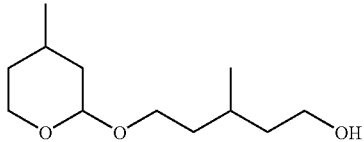

and β-methyl-δ-valerolactone (hereinafter, referred to as "MVL") was found to increase with time. These by-products cause degradation of a hydrogenation catalyst. In addition, in a separation/purification step for MPD after hydrogenation, because the boiling point difference between MVL (boiling point: 231° C./0.1 MPa) and MPD (boiling point: 272° C./0.1 MPa) is large, it is possible to separate MVL by distillation of the reaction mixture. On the other hand, because the boiling point of MPAE (boiling point: 276° C./0.1 MPa) and MPD is close, it is actually very difficult to separate MPAE (boiling point: 276° C./0.1 MPa) from MPD by an industrially common distillation column. MPAE is a monohydroxy compound, therefore, when the polymerization reaction of polyester or polyurethane is carried out using MPD having a high content of MPAE, MPAE tends to seal a polymerization end resulting in a problem that molecular weight of polymer does not increase. It is very important, therefore, to enhance the purity of MPD for these uses too. However, in order to enhance the purity of MPD, it is difficult to achieve by simple distillation, it is necessary to decrease the amount of MPAE generated in hydrogenation.

In addition, the method disclosed in Patent Literature 3 is the method characterized by using Raney nickel modified with molybdenum in order to suppress the generation of by-products (MPAE and MVL) that may cause degradation of a hydrogenation catalyst. The method disclosed in Patent Literature 3, however, has a problem that the method can not be substituted by known hydrogenation catalysts to be commonly used such as Raney nickel and Raney cobalt other than this particular Raney nickel (see lower left 15th line to lower right 3rd line, page 2, Patent Literature 3).

In these situations, the object of the present invention, in the production of MPD by hydrogenation of MEP, is to provide an industrially advantageous method for producing high-purity MPD in a high yield by suppressing the generation of by-products such as MPAE and MVL with using a known hydrogenation catalyst to be commonly used other than Raney nickel modified with molybdenum.

Means for Solving the Problem

The present inventors have studied intensively to attain the above object. As a result, surprisingly, we have found that, when MHP is hydrogenated using a hydrogenation catalyst in the presence of a basic compound, subgeneration of MPAE and MVL can be effectively suppressed simultaneously even if the hydrogenation catalyst is not necessarily the Raney nickel modified with molybdenum.

That is, the present invention relates to a method for producing MPD by hydrogenating MHP in the presence of a hydrogenation catalyst wherein the method is characterized by being carried out additionally in the presence of a basic compound.

Advantages of the Invention

According to the present invention, in hydrogenation reaction of MHP, high-purity MPD can be industrially advantageously produced while subgeneration of MPAE and MVL is effectively suppressed and the life of the hydrogenation catalyst is prolonged even without using Raney nickel modified with molybdenum.

DESCRIPTION OF REFERENCE NUMERALS

Figure 1:
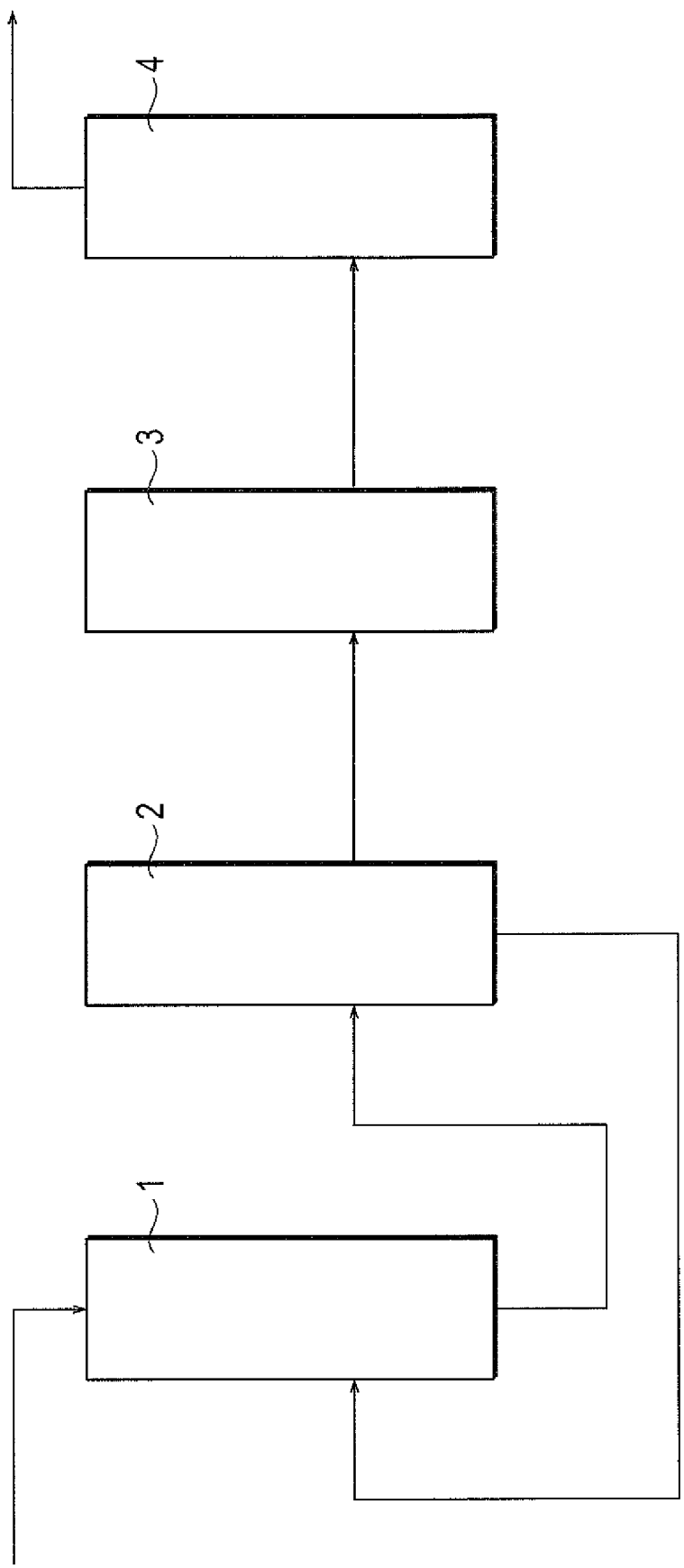
FIGURE 1 is a drawing illustrating the outline of the reaction apparatus used in Example 10.

1: Reactor
2: Solid-Liquid Separator
3: Evaporator
4: Distillation Column

BEST MODE FOR CARRYING OUT THE INVENTION

The present invention relates to a method for producing MPD by hydrogenating MHP in the presence of a hydrogenation catalyst wherein the method is characterized by being carried out additionally in the presence of a basic compound.

As the hydrogenation catalyst that can be used for the present invention, a known catalyst to be used for hydrogenation of an aldehyde (for example, see "hannoubetu jituyou shokubai" ("practical catalyst for each reaction") published by Kagaku Kougyousha, 1970, P. 111-141, p. 176-180) can be used, for example, nickel, Raney nickel, palladium, Raney cobalt, copper-chromium oxide, platinum and ruthenium are included. From the standpoints of easy handling and economy, Raney nickel and Raney cobalt are particularly preferable among these hydrogenation catalysts. As a hydrogenation catalyst, either of a homogeneous catalyst or a heterogeneous catalyst may be used, but a heterogeneous catalyst is preferable from the standpoint of easiness in removal of the hydrogenation catalyst after the reaction. A heterogeneous catalyst supported by a carrier such as activated carbon, diatomaceous earth, silica and alumina may be used. Such a heterogeneous catalyst may be modified with chromium, molybdenum, aluminum, tungsten or the like. A hydrogenation catalyst may be used alone or in combination of two or more. Usually, the amount of a hydrogenation catalyst to be used is preferably in the range of 0.01 to 3% by mass and more preferably in the range of 0.1 to 1% by mass relative to the total amount of the reaction solution in a reactor. A hydrogenation catalyst suspended in water may be used.

The basic compound to be used in the present invention is not particularly limited as long as it is a basic inorganic compound or a basic organic compound that has no adverse effect on hydrogenation. Such a basic inorganic compound includes, for example, an alkaline metal hydroxide such as sodium hydroxide and potassium hydroxide; an alkaline metal carbonate such as sodium carbonate and potassium carbonate; an alkaline metal hydrogen carbonate such as sodium hydrogen carbonate; an alkaline earth metal hydroxide such as magnesium hydroxide and calcium hydroxide; and an alkaline metal alkoxide such as sodium methoxide. In addition, the basic organic compound includes, for example, a tertiary amine such as triethylamine, tributylamine, trioctylamine and triethanolamine. Among these compounds, particularly, from the standpoint of suppressing subgeneration of MPAE, inorganic compounds, especially sodium carbonate and sodium hydroxide are preferable. The amount of a basic compound to be used is preferably in the range of 150 ppm to 5,000 ppm (mass ratio), more preferably in the range of 150 ppm to 1,000 ppm (mass ratio) relative to the total amount of the reaction solution in a reactor. The amount of a basic compound to be used less than 150 ppm (mass ratio) relative to the total amount of the reaction solution in a reactor tends to result in minor effect for suppressing subgeneration of MPAE and MVL at the same time, whereas the amount of a basic compound to be used more than 5,000 ppm (mass ratio) relative to the total amount of the reaction solution in a reactor tends to cause a side reaction such as an aldol reaction. A solid basic compound may be added to a reaction solution as it is, but addition by solution is preferably adopted in order to avoid uneven concentration distribution in a reaction solution. The solvent to be used for a solution is not particularly limited as long as it dissolves a basic compound sufficiently and does not react with a reaction product, and includes, for example, an alcohol such as methanol, ethanol, 2-propanol and MPD and water. The concentration of a basic compound in a solution is not particularly limited, but, usually it is preferably in the range of 5 to 70% by mass from the standpoint of handling. A liquid basic compound may be added to a reaction solution as it is.

Incidentally, the concentration of a basic compound in a reaction solution can be calculated by taking out part of the reaction solution and titrating it with an acid standard solution of which the concentration is known (for example, 0.01 mol/L aqueous solution of hydrochloric acid).

The present invention can be carried out either in the presence or in the absence of a solvent. The solvent is not particularly limited as long as it has no adverse effect on hydrogenation, and includes an alcohol such as methanol, ethanol, n-propyl alcohol, isopropyl alcohol, n-butyl alcohol, isopentyl alcohol and MPD; an ether such as tetrahydrofuran and dioxane. These solvents may be used alone or in combination of two or more. Among these solvents, MPD is preferably used. The MPD produced in the present invention may be used as the above MPD. When a solvent is used, usually, the amount of a solvent to be used is preferably in the range of 10 to 95% by mass relative to the total amount of the reaction solution.

The reaction temperature for the present invention is not particularly limited, but usually it is preferably in the range of 50 to 200° C., more preferably in the range of 60 to 150° C. from the standpoints of stability of MHP, activity of a hydrogenation catalyst, economy and handling.

The reaction pressure is not particularly limited, but usually it is preferably in the range of 0 to 20 MPa (gauge pressure), more preferably 0.1 to 2 MPa (gauge pressure) from the standpoints of handling, safety, reaction efficiency and economy.

Usually, the reaction time (retention time) is preferably in the range of 1 to 50 hours, more preferably in the range of 2 to 30 hours from the standpoint of suppressing generation of by-products such as MPAE and MVL.

When a heterogeneous hydrogenation catalyst is used, the usage type of such a catalyst in reaction system is optional and includes, for example, a suspension tank type, a fixed-bed type and a fluidized-bed type. When a homogeneous catalyst is used, a reactor such as a stirred reactor, a bubble-column reactor and a distillation-column reactor may be used. In addition, for either a heterogeneous or homogeneous hydrogenation catalyst, any process of a batch process, a semibatch process and a continuous process may be used, but it is preferable to use a continuous process in view of production efficiency.

In a batch process, the reaction can be carried out, for example, by charging a hydrogenation catalyst, MHP, a basic compound and a solvent as needed at a time in a reactor under an atmosphere of hydrogen and stirring them at a specified temperature and a specified pressure for a specified time. In a semibatch process, for example, a hydrogenation catalyst, a basic compound and a solvent as needed are charged in a reactor under an atmosphere of hydrogen and mixed at a specified temperature and a specified pressure. First, part of MHP is supplied to the reactor to initiate the reaction and then the remainder of the MHP is introduced continuously or intermittently to carry out the reaction for a specified time.

In a continuous process, for example, MHP, a basic compound and a solvent as needed are each supplied continuously or intermittently to a reactor at a specified temperature and a specified pressure in the presence of a hydrogenation catalyst while stirring for a specified time. And, the reaction can be carried out while taking out the obtained reaction mixture continuously or intermittently through a reactor outlet during the reaction.

Separation/purification of MPD from the reaction mixture obtained in the above process can be carried out by a common method for separation/purification of an organic compound. For example, high-purity MPD can be obtained by separating a hydrogenation catalyst by a means such as filtration, sedimentation and centrifugal separation and then distilling the residue. Incidentally, the reason why such high-purity MPD can be obtained through distillation is that subgeneration amount of MPAE is suppressed to an extremely low level in the hydrogenation of the present invention (seethe following examples). In addition, when a hydrogenation catalyst is separated, it is very desirable to reuse the separated hydrogenation catalyst for the hydrogenation of the present invention in view of the production cost.

The MHP to be used in the present invention can be produced by a known method (see Patent Literatures 1 and 2). For example, it can be produced by reacting IPEA with carbon monoxide and hydrogen at 60 to 150° C. and 1 to 20 MPa in the presence of a rhodium compound such as $Rh_4(CO)_{12}$ or $Rh(acac)(CO)_2$. The IPEA is industrially available and also can be produced by the following method. For example, IPEA can be produced by reacting isobutene and a 37% by mass aqueous formaldehyde at preferably 5 to 50 MPa and 235 to 400° C. (see JP-B-47-47362).

EXAMPLES

The present invention is described more specifically with reference to the following examples, to which, however, the present invention is not limited at all. Incidentally, the gas chromatographic analysis in each example and comparative example is conducted by the following procedures.

[Gas Chromatographic Analysis]
Analytical instrument: GC-14A (made by Shimadzu Corporation)
Column: CBP-20 (length: 50 m) (made by J&W Scientific Inc.)
Analytical conditions: injection temperature: 240° C. detection temperature: 240° C.
Heating conditions: 80° C.(retention for 0 minutes)→(heating at 8° C./minute)→220° C.(retention for 10 minutes)

Example 1

Into a magnetic stirrer type autoclave having an internal volume of 500 ml equipped with a hydrogen gas supply opening, a raw material supply opening, a thermometer and a sampling opening, 2 g (about 1 g as unmodified Raney nickel; about 0.67% by mass relative to the reaction solution) of unmodified Raney nickel suspended in water [B-113W (trade name) made by Degussa], 75 g (0.647 mol) of MHP, 75 g (0.636 mol) of MPD and 1.87 ml (equivalent to 500 ppm relative to the total mass of the charged reactants in sodium hydroxide equivalent) of 1 mol/L aqueous solution of sodium hydroxide, was charged. Thus obtained reaction solution was found to have a pH of 10.9 by the measurement of pH meter. After replacing the reaction system with nitrogen gas (0.29 MPa; gauge pressure) 3 times while stirring the reaction solution at 800 rpm, the system was replaced with hydrogen gas (0.29 MPa; gauge pressure) 3 times, and heated to 120° C. while keeping the pressure at 0.88 MPa (gauge pressure) with hydrogen gas and then subjected to reaction for 5 hours. Incidentally, during the reaction, the off gas rate was 10 L/hour and the hydrogen pressure in the reaction system was kept at 0.88 MPa (gauge pressure) After termination of the reaction, the reaction mixture was found to have a pH of 8.4 by the measurement of pH meter. In addition, the obtained reaction mixture was analyzed with gas chromatography after the reaction. The results are shown in Table 2.

Examples 2 to 6 and Comparative Examples 1 to 3

Reaction and analysis were conducted similarly to in Example 1 except that the conditions were set as shown in Table 1. Each result is shown in Table 2.

TABLE 1

| | Catalyst | Amount[2] of addition of aqueous solution of sodium hydroxide (ppm) | Reaction temperature (° C.) | Reaction time (hour) |
|---|---|---|---|---|
| Example 1 | B-113W[1] | 500 | 120 | 5 |
| Example 2 | B-113W[1] | 100 | 120 | 5 |
| Example 3 | B-113W[1] | 10 | 120 | 5 |
| Com. Ex. 1 | B-113W[1] | 0 | 120 | 5 |
| Example 4 | B-2112Z[1] | 150 | 140 | 5 |
| Example 5 | B-2112Z[1] | 100 | 140 | 5 |
| Com. Ex. 2 | B-2112Z[1] | 0 | 140 | 5 |
| Example 6 | BK-113AW[1] | 150 | 120 | 2 |
| Com. Ex. 3 | BK-113AW[1] | 0 | 120 | 2 |

B-113W (trade name); unmodified Raney nickel
B-2112Z (trade name); unmodified Raney cobalt
BK-113AW (trade name); Raney nickel modified with 1.2% by mass molybdenum
[1]Made by Degussa
[2]Amount of addition relative to the total amount of the reactants in the reactor, in terms of sodium hydroxide
Com. Ex.: Comparative Example

TABLE 2

| | Conversion (%) | Selectivity (%) | | |
|---|---|---|---|---|
| | | MPD | MPAE | MVL |
| Example 1 | 76.1 | 94.1 | 1.1 | 2.0 |
| Example 2 | 89.3 | 93.8 | 2.5 | 3.1 |
| Example 3 | 85.2 | 90.2 | 2.7 | 5.5 |
| Comparative Example 1 | 75.4 | 84.3 | 4.3 | 8.4 |
| Example 4 | 97.9 | 96.5 | 1.7 | 1.9 |
| Example 5 | 93.6 | 93.9 | 3.4 | 1.5 |
| Comparative Example 2 | 93.3 | 82.7 | 13.7 | 3.1 |
| Example 6 | 98.7 | 94.8 | 0.1 | 3.3 |
| Comparative Example 3 | 98.2 | 88.9 | 3.6 | 6.0 |

Example 7

Reaction and analysis were conducted similarly to in Example 1 except that 0.38 ml (equivalent to 250 ppm relative to the total mass of the charged reactants in sodium carbonate equivalent) of 10% aqueous solution of sodium carbonate was used instead of 1.87 ml (equivalent to 500 ppm relative to the total mass of the charged reactants in sodium hydroxide equivalent) of 1 mol/L aqueous solution of sodium hydroxide. As a result, the conversion was 83.1% and the selectivities of MPD, MPAE and MVL were 93.2%, 2.1% and 2.5% respectively.

Example 8

Reaction and analysis were conducted similarly to in Example 1 except that 0.54 ml (equivalent to 100 ppm relative to the total mass of the charged reactants in potassium hydroxide equivalent) of 0.5 mol/L aqueous solution of potassium hydroxide was used instead of 1.87 ml (equivalent to 500 ppm relative to the total mass of the charged reactants in sodium hydroxide equivalent) of 1 mol/L aqueous solution of sodium hydroxide. As a result, the conversion was 86.8% and the selectivities of MPD, MPAE and MVL were 93.8%, 2.0% and 2.9% respectively.

Example 9

Reaction and analysis were conducted similarly to in Example 1 except that 0.067 ml (equivalent to 500 ppm relative to the total mass of the charged reactants) of triethanolamine was used instead of 1.87 ml (equivalent to 500 ppm relative to the total mass of the charged reactants in sodium hydroxide equivalent) of 1 mol/L aqueous solution of sodium hydroxide. As a result, the conversion was 84.6% and the selectivities of MPD, MPAE and MVL were 94.3%, 3.3% and 1.7% respectively.

Example 10

The present invention was carried out as follows by a continuous process using the facilities shown in FIGURE 1.

Into a reactor 1 having an internal volume of 1 m$^3$, B-113AW of Raney nickel modified with 1.2% by mass molybdenum (concentration in the reaction solution: 0.5% by mass) and MHP were charged. The reactor 1 was kept at 0.88 MPa (gauge pressure) with hydrogen gas and hydrogenation was initiated at a reaction temperature of 120° C. When the conversion of MHP became 98% and more, MHP was supplied continuously at a rate of 30 L/hour and also a 25% aqueous solution of sodium hydroxide was supplied intermittently to the reactor 1 so that the concentration of the sodium hydroxide in the reaction solution was kept in the range of 150 to 250 ppm (by mass) and part of the obtained reaction mixture was taken out and the BK-113AW was separated and recovered by a solid-liquid separator 2, and returned to the reactor 1 to reuse in the present reaction. Incidentally, the retention time of the reaction solution in the reactor 1 was 24 hours. Incidentally, the gas chromatography measurement showed that the composition of the liquid phase in the reactor 1 was MPD: 92.3%, MPAE: 0.1% and MVL: 2.0%. On the other hand, the reaction mixture separated from the BK-113AW by the solid-liquid separator 2 was sufficiently rectified through an evaporator 3 and a distillation column 4. The gas chromatography measurement showed that the composition of the distillate from the top of the distillation column 4 was MPD: 99.1%, MPAE: 0.1% and NVL: not detected. After such continuous hydrogenation was continued for 6 months, no evidence of activity degradation of the hydrogenation catalyst used repeatedly was found and the conversion was kept at 99% from the first day of the reaction.

From the results of Examples 1 to 9 and Comparative Examples 1 to 3, addition of a basic compound in the hydrogenation of MHP has enabled the production of higher-purity MPD by effectively reducing by-products such as MPAE and MVL compared with the case of no addition of the basic compound. In addition, from the result of Example 10, it can be understood that addition of a basic compound in the hydrogenation of MHP enables effective suppression of subgeneration of MPAE and MVL that cause deactivation of a hydrogenation catalyst and thus can keep the activity of the hydrogenation catalyst high for a long period.

The invention claimed is:

1. A method for producing 3-methyl-1,5-pentanediol by hydrogenating 2-hydroxy-4-methyltetrahydropyran in the presence of a hydrogenation catalyst, wherein the method is characterized by carrying out the hydrogenation additionally in the presence of a basic compound.

* * * * *